United States Patent
Dobos et al.

(10) Patent No.: US 6,168,800 B1
(45) Date of Patent: Jan. 2, 2001

(54) ANTIMCROBIAL MULTI-LAYER ISLAND DRESSING

(75) Inventors: John A. Dobos, East Amherst; Ronald D. Mabry, Orchard Park, both of NY (US)

(73) Assignee: Medwrap Corporation, Amherst, NY (US)

( * ) Notice: Under 35 U.S.C. 154(b), the term of this patent shall be extended for 0 days.

(21) Appl. No.: 09/137,040

(22) Filed: Aug. 20, 1998

(51) Int. Cl.$^7$ .................................................. A61F 13/00
(52) U.S. Cl. ........................ 424/405; 424/402; 424/409; 424/443; 424/445; 424/446
(58) Field of Search .................... 424/402, 405, 424/409, 443, 445, 446

(56) References Cited

U.S. PATENT DOCUMENTS

| | | | |
|---|---|---|---|
| 3,929,135 | 12/1975 | Thompson | 128/287 |
| 4,317,792 | 3/1982 | Raley et al. | 264/504 |
| 4,341,207 | 7/1982 | Steer et al. | 128/155 |
| 4,456,570 | 6/1984 | Thomas et al. | 264/22 |
| 4,499,896 | 2/1985 | Heinecke | 128/156 |
| 4,535,020 | 8/1985 | Thomas | 428/131 |
| 4,643,180 | 2/1987 | Feld | 128/156 |
| 4,728,323 | 3/1988 | Matson | 604/304 |
| 4,997,425 | 3/1991 | Shioya | 604/304 |
| 5,009,224 | 4/1991 | Cole | 128/156 |
| 5,010,883 | 4/1991 | Rawlings et al. | 128/155 |
| 5,069,907 | 12/1991 | Mixon et al. | 424/445 |
| 5,106,362 | 4/1992 | Gilman | 602/47 |
| 5,167,613 | 12/1992 | Karami et al. | 602/42 |
| 5,180,605 | 1/1993 | Milner | 427/2 |
| 5,465,735 | 11/1995 | Patel | 128/888 |
| 5,569,207 | * 10/1996 | Gisselberg et al. | 604/175 |
| 5,632,731 | 5/1997 | Patel | 602/59 |
| 5,637,080 | 6/1997 | Geng | 602/58 |
| 5,681,579 | 10/1997 | Freeman | 424/448 |
| 5,725,867 | 3/1998 | Mixon | 424/402 |
| 5,849,805 | * 12/1998 | Dyer | 521/64 |
| 5,980,620 | * 11/1999 | Brodie et al. | 106/15.05 |

\* cited by examiner

*Primary Examiner*—S. Mark Clardy
*Assistant Examiner*—Kathryne E. Shelborne
(74) *Attorney, Agent, or Firm*—Howard M. Ellis; Marianne Fuierer

(57) ABSTRACT

An antimicrobial multi-layer island dressing including an inner absorbent assembly having a first layer comprising a wound contacting non-absorbent, non-adhering porous polymeric film which is impregnated with a broad spectrum antimicrobial agent, a second layer comprising a semipermeable continuous polymeric film joined to the first layer to form a sealed interior reservoir compartment, an absorbent material positioned within the interior reservoir compartment to collect discharged exudate from a wound, and an outer layer extending beyond the peripheral edges of the inner absorbent assembly, the outer layer having at least a portion coated with an adhesive material for adhering the island dressing to the wound area. The preferred antimicrobial agent is 2,4,4'-trichloro-2'-hydroxydiphenyl ether and may be present in an amount from about 0.01 to about 25 percent by weight of film material.

31 Claims, 6 Drawing Sheets

ANTIMCROBIAL MULTI-LAYER ISLAND DRESSING

TECHNICAL FIELD

This invention relates generally to a medical dressing and more specifically to a multi-layer island dressing which directly contacts a wound with a broad spectrum antimicrobial agent.

BACKGROUND OF INVENTION

During wound healing, a properly designed and applied dressing can be of tremendous benefit in promoting healing and ensuring comfort. However, if a wound is contaminated with microorganisms such as bacteria or fungi, the natural healing process may be greatly reduced.

The natural healing process includes an inflammatory response wherein wound exudate containing neutrophils and monocytes emigrates into injured tissue. Neutrophil infiltration usually ceases within a few days if wound contamination has not occurred. However, substantial wound contamination will provoke a persistent neutrophil-rich inflammatory response. Additional neutrophils will be attracted to such contaminated wounds to cleanse the wounded area. If excessive microorganisms have lodged in the wound bed, neutrophils may cause further tissue damage by attempting to clear the contaminants with the release of enzymes and toxic oxygen products. As such, it is beneficial to apply an antimicrobial agent to the wound site to minimize neutrophil infiltration.

Heretofore, several methods have been used in wound management including, directly applying antimicrobial agents in a carrier ointment or the ingesting of systemic antibiotics. Systemic antibiotics do not necessarily treat the wound itself, but they prevent the spread of infection. It should be noted that in a contaminated wound blood-borne antibiotics are of limited value because tissues that are dead and without a blood supply are inaccessible to systemic antimicrobials. Even viable areas of localized infection are soon walled off from surrounding tissues and therefore are not treatable with ingested antibiotics.

It is known that ointments containing an antimicrobial agent in a liquid or white petrolatum vehicle may be effective in preventing infection when spread directly on the wound. However, these ointments are very greasy and remnants of the ointment may stay in the wound bed thereby slowing the healing process.

Several medical dressings have been proposed which provide an absorbent layer incorporating an antimicrobial agent therein. The absorbent material collects the increased exudate from a contaminated wound site while inhibiting growth of bacteria that may be washed from the wound site into the absorbent material. However, in these dressings the absorbent material is not in direct contact with the wound site. For example, U.S. Pat. Nos. 5,106,362 and 5,167,613 propose dressings with the incorporation of an antimicrobial agent into an absorbent material, but these dressings are only effective on that bacteria which is physically washed into the absorbent material.

If bacteria growth is not inhibited the inflammatory response will continue and in some dressings the absorbent material inserts are unable to accommodate the excess fluids. When this occurs excess exudate is allowed to seep back to the wound bed with no defense for inhibiting the growth of bacteria. The inability to retain excess fluid may be exhibited in the dressing described in U.S. Pat. No. 4,499,896.

U.S. Pat. No 3,929,135 discloses an absorptive structure having a polymeric film comprising tapered capillaries which allow fluid to flow through the capillaries but reduce backflow seepage of exudate to the wound site. This one-way porous film may help contain the excess exudate but does not provide any antimicrobial defenses in a contaminated wound.

U.S. Pat. No. 4,728,323 discloses a substrate coated with an antimicrobially effective film of silver salt, but does not provide absorbent means for excess wound exudate that usually occurs in an infected or contaminated wound. Similarly, U.S. Pat. Nos. 5,614,310 and 4,643,180 provide for dressings having an antimicrobial agent dispersed in an adhesive material which is coated on another surface but these dressings may leave a residue in the wound that inhibits the healing process.

U.S. Pat. Nos. 4,341,207 and 4,997,425 disclose dressings which apply an absorbent material directly to the wound wherein the absorbent material incorporates an antimicrobial agent. However, the possibility of absorbent materials adhering to the healing tissue during scab formation detracts from using these dressings. When the dressing is removed, the healing process may be hindered by causing a reinjury which may produce a larger and unsightly scar.

U.S. Pat. No. 5,681,579 describes a dressing having an antimicrobial agent mixed in with a hydrocolloid material which may be subsequently incorporated into a polymer film or coated on a polymeric surface. However, there is the acknowledged disadvantage of using hydrocolloids, that being they are known to breakdown and may even produce a residue of varying colors and/or a possible foul odor. These adverse results could be confused with an infectious process or more important hide a serious wound infection.

Accordingly, what is needed is a wound dressing that contacts the wound site directly with an antimicrobial agent without leaving residue from foreign material such as adhesive or absorbent material in the wound bed, provides an absorbent material to collect exudate discharge from the wound which does not directly contact the wound surface, prevents backflow of exudate from the absorbent material to the wound bed, and provides a waterproof/bacteria barrier to protect the wound from external contaminants.

SUMMARY OF INVENTION

Terms

For purposes of this invention, the terms and expressions below, appearing in the specifications and claims, are intended to have the following meanings:

"Wound" as used herein means a surgical incision, laceration or any other injury that needs to be protected by the present invention.

"Semipermeable film" as used herein means a film that is permeable to water vapor and oxygen but is impermeable to liquids and bacteria.

"Exudate" as used herein means fluid, cells or other substances that have been slowly exuded, or discharged, from cells or blood vessels through small pores or breaks in cell membranes.

The present invention meets the aforementioned needs by providing an interactive island dressing that optimizes the healing environment by introducing an antimicrobial agent that directly contacts the wound bed, will not mask a serious wound infection or leave residue from foreign materials such as adhesive or absorbent material in the wound bed. In addition this interactive dressing provides for a continuous second layer which prevents contamination from exterior sources such as liquids or bacteria but still allows for offgasing of wound healing gases and water vapor. The first and second layer are joined to form a fluid reservoir wherein an absorbent material insert is positioned and sealed therein to accommodate excess wound exudate. The absorbent material is maintained away from direct contact with the wound. The interactive island dressing is secured to the wound area by an outer layer having a bottom surface coated with adhesive on at least opposing peripheral margins extending beyond the absorbent assembly.

It is a further object of the present invention to provide a non-absorbent, non-adhering porous polymeric film which is impregnated with an antimicrobial agent wherein the antimicrobial agent is incorporated directly into the polymer's molecular structure and will not wash or wear off, in contrast to a surface coating of antimicrobial agent.

It is still a further object of the present invention to provide a first layer comprising a non-absorbent, non-adhering one-way porous polymeric film having a plurality of tapered protuberances. The one-way porous polymeric first layer is joined to a second layer to form a sealed fluid reservoir compartment having an absorbent material therein. The one-way pores have a generally funnel-like configuration and they narrow and extend in the direction of the interior of the fluid reservoir. This configuration allows wound exudate to discharge into the fluid reservoir while reducing backflow of exudate from the reservoir to the wound site. The second layer is fabricated from a gas and water vapor permeable, liquid impermeable continuous polymeric film so that wound gas can escape from the wound site but contamination from liquid or bacteria cannot gain access to the wound. The first layer is sealed to the second layer along their peripheral edges thereby providing an essentially closed receptacle that holds wound exudate. This essentially closed receptacle is advantageous because when the dressing is removed from the patient any excess fluid contained in the reservoir will not escape and spill on the patient or care giver.

The objects of the present invention are achieved by a multi-layer medical island dressing providing antimicrobial protection comprising:
a) an absorbent assembly including:
   i) a non-absorbent, non-adhering first layer comprising a porous flexible polymeric film, the first layer having a wound contacting side and an opposing non-wound contacting side, the film having impregnated therethrough a sufficient amount of an antimicrobial agent to effectively control an infection and/or inhibit the growth of microorganisms in a wound;
   ii) a second layer comprising a semipermeable continuous polymeric film, the second layer joined to the non-wound contacting side of the first layer to form a sealed interior reservoir compartment;
   iii) an absorbent material positioned between the first and second layer in the sealed interior reservoir compartment for retaining exudate discharged from the wound; and
b) an outer layer comprising a gas permeable continuous polymeric film, the outer layer having a bottom surface for contacting an area around the wound and an opposing top surface, the bottom surface positioned adjacent to the second layer of the absorbent assembly and extending beyond the absorbent assembly, the outer layer having at least a portion of the bottom surface coated with an adhesive material for adhering to the area surrounding the wound.

In an alternative preferred embodiment, the non-absorbent, non-adhering first layer which comprises a porous, flexible polymeric film impregnated with an antimicrobial agent may be fabricated from a one-way polymeric film having a plurality of tapered protuberances or conical shaped pores that allow wound exudate to flow through the pores but substantially restrict backflow of exudate to the wound site. The tapered protuberances have a generally funnel-like configuration which narrow in the direction of the fluid reservoir. The one-way porous film is impregnated with an effective amount of an antimicrobial agent such that the growth of microorganisms is substantially inhibited.

In another preferred embodiment the multi-layer medical island dressing comprises:
a) a non-absorbent, non-adhering first layer comprising a porous flexible polymeric film, the first layer having a wound contacting side and an opposing non-wound contacting side, the film having impregnated therethrough a sufficient amount of an antimicrobial agent to effectively control an infection and/or inhibit the growth of bacteria in a wound;
b) an outer layer comprising a semipermeable continuous polymeric film, the outer layer having a bottom surface for contacting an area surrounding the wound and an opposing top surface, the bottom surface of the outer layer joined to the non-wound contacting side of the first layer to form a sealed interior reservoir compartment, the outer layer extending beyond the first layer and having at least a portion of the bottom surface coated with an adhesive material for adhering to the area surrounding the wound.

The absorbent assembly may further comprise an absorbent material positioned between the first and outer layer in the sealed interior reservoir compartment for retaining exudate from the wound.

In this embodiment the porous polymeric film impregnated with an antimicrobial agent may be fabricated from a one-way polymeric film having tapered protuberances or conical shaped apertures that allow wound exudate to flow through the pores but restrict backflow of exudate to the wound site. The one-way porous film is impregnated with an effective amount of the antimicrobial agent such that the growth of microorganisms is substantially inhibited and infections are controlled.

BRIEF DESCRIPTION OF DRAWINGS

The present invention will now be described by way of example with reference to the accompanying drawings in which.

DESCRIPTION OF THE PREFERRED EMBODIMENTS

The preferred embodiments of the present invention and their advantages are best understood by referring to FIGS. 1–12 of the drawings, like numerals being used for like and corresponding parts of the various drawings.

As was heretofore mentioned, the present invention is directed to a multi-layer island dressing which provides an interactive healing environment by releasing an antimicrobial agent from a wound contacting porous polymeric film. In addition, the dressing provides a fluid reservoir for the retention of wound exudate, a liquid impermeable barrier film for protection from contamination and an extended cover which adheres the dressing to the wound area while facilitating the transport of gases to and from the wound during the healing process.

Figure 1:
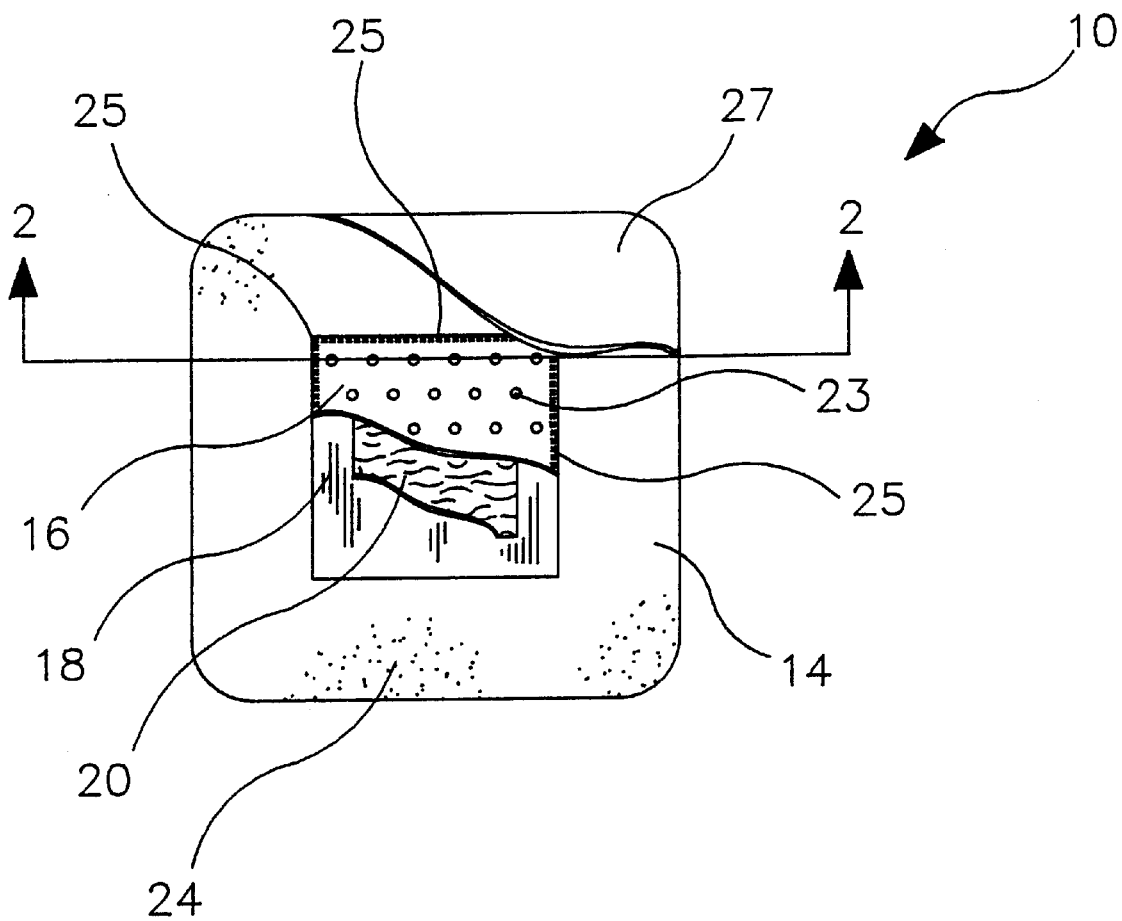
FIG. 1 is a bottom view of a multi-layer island dressing for placement on the wound.
Figure 2:
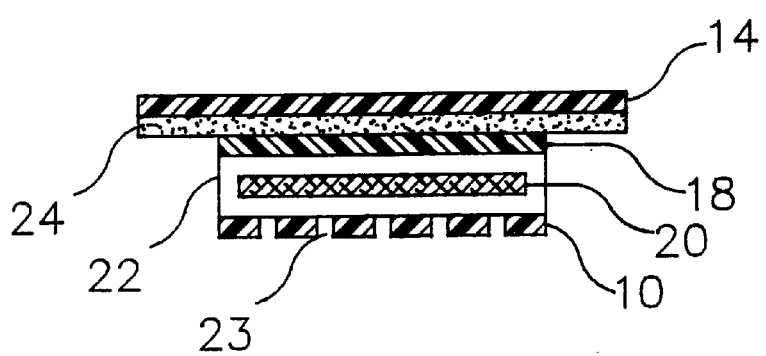
FIG. 2 is an enlarged cross-sectional view of the multi-layer dressing taken along lines 2—2 of FIG. 1.
Figure 3:
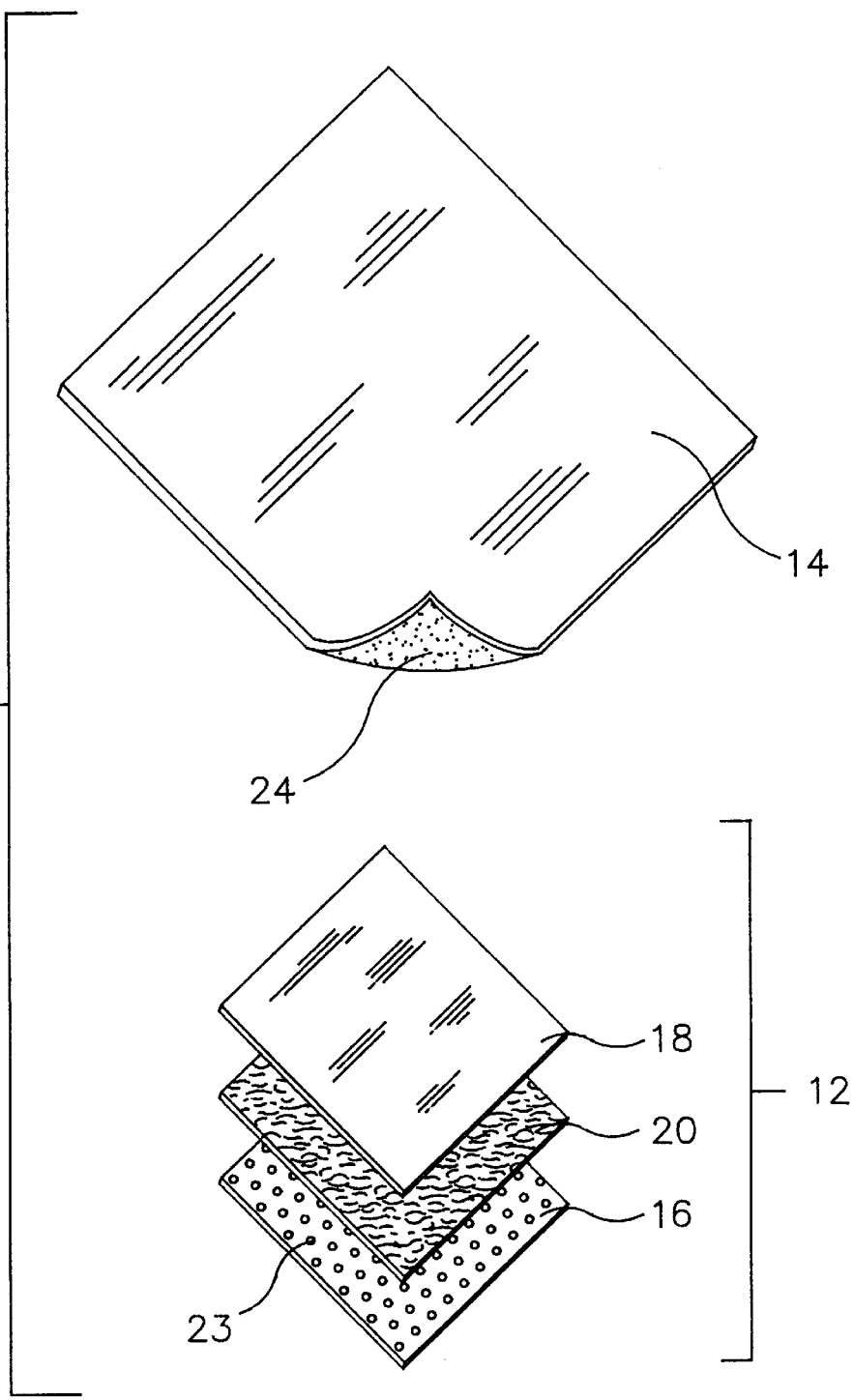
FIG. 3 is an exploded perspective view of a multi-layer island dressing before the fluid reservoir is formed.

With reference to FIGS. 1–3, the multi-layer island dressing 10 of this invention comprises an inner absorbent assembly 12 and an outer layer 14. The absorbent assembly 12 comprises a non-absorbent, non-adhering porous polymeric film first layer 16, a liquid impermeable, gas permeable continuous polymeric second layer 18, a fluid reservoir 22 formed by the joining of the first layer to the second layer and an absorbent material layer 20 positioned in the fluid reservoir. An outer layer 14 comprises a gas permeable continuous polymeric film which extends beyond the margins of absorbent assembly 12 and provides an adhesive surface for adhering to the wound area.

As shown in FIG. 1 the first layer 16 comprises a porous non-absorbent, non-adhering polymeric film that is positioned directly on the wound. By "porous" is meant that the polymeric film is either a web, net, perforated film or film having one-way tapered protuberances. The porous film employed in the present invention may be flexible, conformable to anatomical shapes and provide a pathway for passage of wound exudate away from the wound bed. The pores or perforations should be sufficient in size to permit wound exudate to move away from the wound without pooling at the wound bed. For example, there may be on the order of 40 to 1400 perforations per square inch having a diameter that is determined by the number of perforations. Larger pore diameters are possible with reduced quantities of perforations per square inch. Suitable materials include polymeric materials such as low and high density polyethylene, polypropylene, polyurethane, polybutadiene, polyester, polyvinyl chloride, polyolefin copolymers such as ethylene-vinyl acetate copolymers and the like. A non-absorbing, non-adhering polymeric film will allow the removal of the dressing without reinjury to a healing wound. In a particularly preferred embodiment, the polymeric material is either polyethylene or polyurethane having a thickness from about 0.5 to about 3 mil and preferably from about 1 to about 2 mil.

The present invention provides for the incorporation of an antimicrobial agent directly into a synthetic polymer which is used to fabricate the porous polymeric film of the first layer. The antimicrobial agent provides resistance to the growth of bacteria and fungi and functions to inhibit bacteria growth at the wound bed. It further functions to inhibit bacteria growth as the wound exudate passes through the porous pathways away from the wound. Any antimicrobial agent that is compatible with the virgin polymer and will retain its activity after the film fabrication process may be used in the present invention.

A large number of antimicrobial agents are contemplated for use in the present invention including:

i) metal salts such as silver, copper salts;

ii) typical antibiotics such as neomycin, soframycin, bacitracin;

iii) quaternary ammonium compounds such as centrimide; and iv) 2,4,4'-trichloro-2'-hydroxydiphenyl ether and 5-chloro-2 -(2,4-dichlorophenoxy) phenol available from Microban Products Company, Huntersville, N.C.

In the preferred embodiment, the antimicrobial agent of choice is 2,4,4'-trichloro-2'-hydroxydiphenyl ether which provides a broad spectrum antimicrobial protection effective against a wide range of Gram positive and Gram negative bacteria and fungi. By incorporating 2,4,4'-trichloro-2'hydroxydiphenyl ether into the synthetic polymer, it is directly incorporated into the polymer's molecular structure and essentially not wear or wash off. While not wishing to be bound by any particular theory of operation, it is believed that the antimicrobial agent is slowly released during the lifetime of the product by a mechanism that allows some of antimicrobial agent to migrate to the surface of the polymeric film from the interior of the film when the antimicrobial agent has been depleted on the surface. As such, the antimicrobial agent migrating to the surface of the porous polymeric film will provide continued protection for the life of the dressing.

The porous film may be impregnated with an effective amount of an antimicrobial agent such that the growth of microorganisms is substantially inhibited. The antimicrobial agent is preferably present in the porous polymeric film in an amount from about 0.01% to about 25% by weight of the polymeric material, more preferably between about 1 and 10% by weight.

To produce the porous polymeric film impregnated with an antimicrobial agent, the polymeric material and antimicrobial agent are mixed together uniformly and homogeneously. The polymeric film is then formed by procedures known in the art. Examples of such procedures include solvent casting, film injection molding and extrusion techniques such as film blowing. The polymeric film impregnated with the antimicrobial agent is then perforated to provide a fluid path for wound fluid. The perforations may be formed by any suitable means. One such means of perforating the film is by passing the film over a heated roll or alternatively the holes are punched into the film mechanically. Another method of perforating the film is by extruding the film, embossing it on a roll and biaxially orienting the film.

Figure 4:
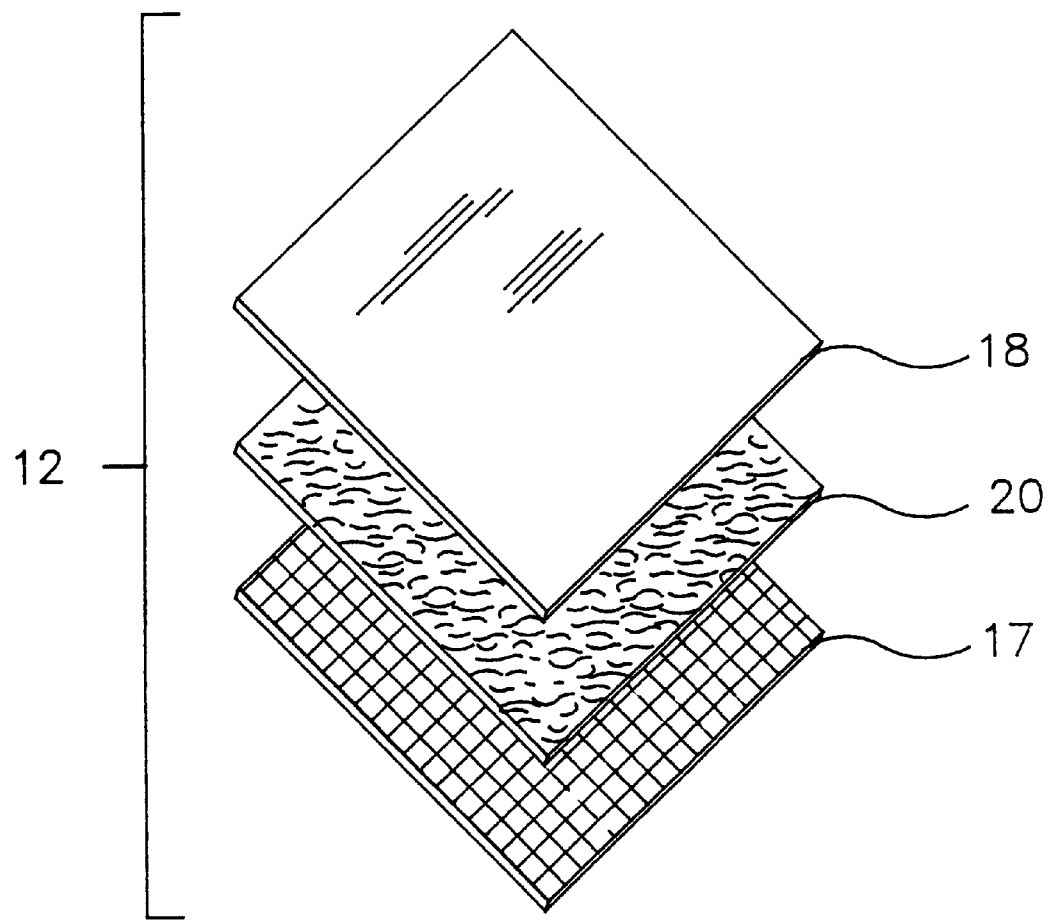
FIG. 4 is an enlarged cross-sectional view of a multi-layer dressing showing an alternative first layer using one-way film with apertures.

In an alternate embodiment of the invention shown in FIG. 4, a first layer 17 which comprises a non-absorbing, non-adhering porous polymeric film impregnated with an antimicrobial agent may be a perforated polyethylene or polypropylene web-type film. This product may be manufactured using extrusion, embossing and orientation processes to prepare a web-type perforated polymeric film. A preferred web-type film is sold under the trademark Delnet, a product of Applied Extrusion Technology. For purposes of the present invention, the polymer used in the fabrication of this web-type film must first be impregnated with an antimicrobial agent.

The absorbent assembly 12 further comprises a second layer 18 which is a liquid impermeable, gas permeable continuous polymeric film. In addition to the second layer providing a barrier to the ingress of liquid and bacteria, it should also permit the transference of air, gas and water vapors to and from the wound site. Any polymeric film that has a moisture vapor permeably of at least 1000 grams per square meter per 24 hours at an 80% relative humidity differential at 40° may be used in the present invention. Suitable polymeric materials for this purpose include polyurethane, a polyolefin such as polyethylene or polypropylene, Saran® (trademark of Dow Chemical), a polyester such as polyethylene terephthalate, etc. The second layer should be relatively thin and be highly conformable. It may for example, be on the order of about 0.4 to about 4.0 mil thick and preferably from about 0.5 to about 2 mil.

The first layer 16 is attached to the second layer 18 on the peripheral edges 25 to form a sealed compartment 22 (shown in FIG. 2) excepting of course the perforations of the first layer which allow wound exudate to enter the sealed compartment. The attachment means for joining the first layer 16 to the second layer 18 along their peripheral edges may include, but not limited to, heat sealing, ultrasonic welding, radio frequency welding and adhesives. The sealed compartment acting as a fluid reservoir provides a confined space for containment of wound fluids. When the dressing is removed the body fluids contained therein will be sufficiently retained in the reservoir to protect medical personal or care givers from coming into contact with bodily fluids that may be contaminated with communicable diseases such as HIV or hepatitis B and C.

Within the sealed fluid reservoir 22 is an absorbent material layer 20. The absorbent material may be secured to the surface of the second layer in the interior of the fluid reservoir. Absorbent materials may comprise materials commonly used in absorptive devices and well known to the art. The reservoir may include fabric materials heretofore employed to retain exudate, including, but not limited to cellulosic materials such as cotton, rayon, and pulp products, superabsorbent webs, foams, fibers and the like. Superabsorbent webs are spun-laced webs made from polyester, polypropylene, or polyethylene. The superabsorbent webs may also be in the form of tissues either single ply or multiply ply and either creped or uncreped. Delnet®, a product of Applied Extrusion Technology provides a web that may be used in preparing a superabsorbent web.

The size, shape and placement of the absorbent material is open to multiple embodiments, depending on the exact and varied requirements of the dressing. The absorbent material should be added in a sufficient amount to absorb excess wound exudate weeping from the wound.

In an alternative embodiment, the absorbent assembly may include a laminated structure that incorporates the non-absorbent, non-adhering porous polymeric first layer, a second layer of semipermeable polymeric film and an absorbent material positioned between the first and second layer in a sealed reservoir compartment. A suitable laminated structure is available as STRATEX™ available from Applied Extrusion Technology wherein the polymeric material used in fabricating the first layer must first be impregnated with an antimicrobial agent chosen from those described above.

The outer layer 14 is a continuous polymeric film that conforms to anatomical surfaces, is gas permeable and has a moisture vapor permeability of at least 1000 grams per square meter per 24 hours at an 80% relative humidity differential at 40° C. The moisture vapor permeability has to be at least as much as the second layer so that excess moisture vapor and gas that escape from the fluid reservoir will also be transmitted through the outer layer. Outer layer 14 acts as a protective layer over the entire absorbent assembly 12. It is adjacent and affixed to the second layer of the absorbent assembly. Any polymeric film that is flexible and has the properties as above noted may be used for the outer layer. Examples of films that are useful include polyurethane, elastomeric polyester, blends of polyester and polyurethane, polyethylene and polypropylene.

Generally the films are from about 0.4 mil to 4 mil in thickness and preferably from about 0.5 to about 2 mil. Additionally, the outer layer may have a fabric-like coating deposited on the top surface.

Outer layer 14 may have a layer of adhesive 24 around at least its peripheral margins to secure the inner absorbent assembly to the central region of the outer layer and for releasible securing to the wound area. The adhesive materials employed may be any of the known medical grade or hypoallergenic adhesives heretofore employed in securing dressings to a skin surface. Such known adhesives include the rubber-based, acrylic, acrylate copolymer, polyvinyl ether and pressure-sensitive adhesives. The thickness of the adhesive layer 24 may be from about 0.2 mil to about 1 mil. It is important that the adhesive provide a firm continuous adhesion to the skin around the wound and will not readily peel away during normal use. Furthermore, the adhesive should easily release without undue pain during the removal of the dressing. Additionally, the adhesive should be of a material that will not unduly impede the healing process or restrict vapor transmission to and from the wound. A preferred high vapor transmission film adhesive is described in U.S. Pat. No. 5,009,224 to Cole, the contents of which are incorporated by reference herein. The adhesive layer allows water vapor to pass at a controlled rate by diffusion of water vapor or gas but prevents water and bacteria from traversing the adhesive film. The moisture vapor transmission of the adhesive should be compatible with that of the outer layer. Preferably, the adhesive should have at least a moisture vapor transmission of about 1000 to 2400 grams per square meter per 24 hour period at 40° C., and 80% humidity differential.

Typically, the multi-layer medical island dressing is applied in the same manner as other wound dressing. A release liner 27 is removed from the adhesive coating 24 and the dressing is pressed against the skin of the patient to cover the wound. The release liner 27 contemplated by the present invention is characterized as providing a substrate to which adhesive layer 24 around the peripheral margins of the bottom surface of outer layer 14 will adhere strong enough to maintain a bond while still allowing easy removal for application of the island dressing to the patient. A peel adhesion suitable for this purpose may, for example, be on the order of from about 0.18 to 0.35 pound per two inches (lb/2"). Examples of release liners include liners made of or coated with polyethylene, polypropylene, silicone coated release papers or polyester films. A preferred release liner is formed from silicone-coated release paper. The release liner should be thick enough to impart sufficient rigidity to the dressing until the dressing is permanently attached to the wound site. Prior to use, the release liner is stripped from the adhesive coating 24 of the dressing so that the dressing may be applied to the skin. The dressing may be packaged in a bacteria-proof package such as paper, plastic or an aluminum foil pouch and sterilization may be achieved in a conventional manner, e.g. by use of gamma irradiation, heat or ethylene oxide.

Figure 5:
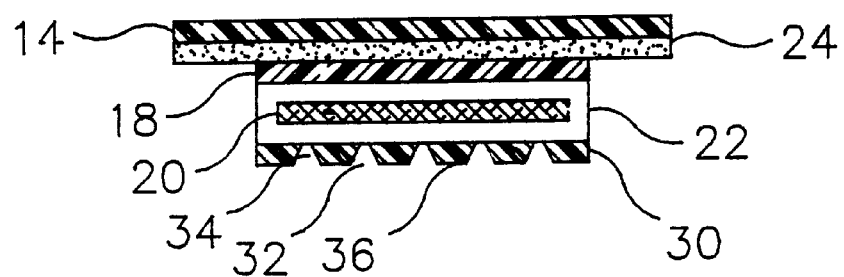
FIG. 5 is an exploded perspective view of an absorbent assembly using web-type polymeric film before the fluid reservoir is formed.

In still another preferred embodiment of the island dressing as shown in FIG. 5, a first layer 30 is comprised of a non-absorbent, non-adhering porous one-way film having tubular protuberances 36. The one-way porous film has a plurality of tapered protuberances having a generally funnel-like configuration which narrow in the direction of the fluid reservoir. These conical pores provide for the passage of wound exudate through the larger pore openings 32 into the fluid reservoir 22 between the first layer 30 and second layer 18 while reducing backflow of fluid from the reservoir to the wound site. The one-way pores because of a unique funnel shape, substantially inhibit the back flow of fluid to the wound site. This is very advantageous for wounds that are producing increased amount of exudate. Isolating wound exudate in the fluid reservoir 22 with the absorbent material 20 in combination with the one-way film eliminates the burdensome and sometime hazardous problem of dealing with body fluids that may contain not only bacteria but also communicable diseases.

Figure 11:
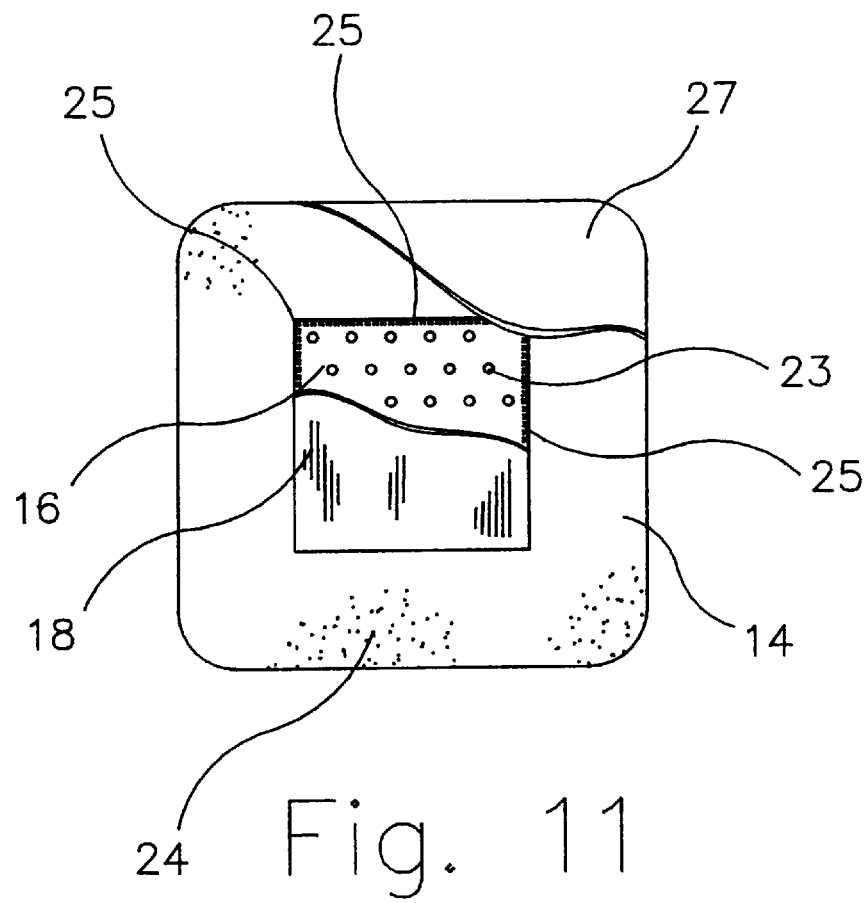
FIG. 11 is a bottom view of a multi-layer island dressing for placement on the wound without an absorbent material insert in the fluid reservoir.

For wounds that are releasing a minimum of exudate, this present invention further contemplates an embodiment wherein the absorbent material insert is not included in the absorbent assembly such as shown in FIG. 11. Instead, the one-way film having tapered capillaries provide pathways for drainage into the fluid reservoir and provide sufficient retention of the exudate by substantially restricting backflow to the wound site. The body fluid is retained in the fluid reservoir and away from the wound bed.

The tapered capillaries can be manufactured by several methods well known in the art. For example, U.S. Pat. Nos. 4,317,792, 4,456,570 and 4,535,020 disclose porous film and methods for their manufacture, the contents of all of such patents are incorporated by reference herein. Briefly, a suitable method includes a heated mold with male elements of the shape and arrangement of the desired tapered apertures. Each male element is secured so that the apex of the shape is extending upward away from the base of the mold. The polymeric material containing an antimicrobial agent homogeneously dispersed therein is brought into contact with the heated mold between the mold and a resilient backing plate. Pressure is applied to the mold and polymeric material thereby forming the tapered protuberances. An alternative way of fabricating the one-way polymeric film includes subjecting a portion of the polymeric material to vacuum forming over an appropriate mold by means well known in the art.

Any polymeric flexible film that provide a substantially one-way flow of fluids and which can be impregnated with an antimicrobial agent may be used in the present invention. One brand of commercially available one-way porous barrier film is from Tredegar Film Products, which offers a porous film having funnel shaped pores and sold under the trademark VisPore®. Preferred grades of the VisPore® films are characterized by an open area of 15 to 26%, with a mesh size ranging from 8 to 40 pores per lineal inch or 88 to 1,840 pores per square inch. The thickness of the porous one-way film can range from about 0.75 mils to 4.0 mils and embossed thickness from about 10 mils to about 50 mils. Some preferred representative grades of the one-way porous film, if impregnated with an antimicrobial agent may include VisPore® 6606, 6605, 6150 and 6178.

The type of fluid being transmitted through the one-way film will be a factor in determining the appropriate mesh and pore size for the most effective passage of fluid and retention of fluid in the fluid reservoir. For many applications involving body fluids, preferably VisPore® 6606 grade film may be effective in reducing backflow of wound exudate from the fluid reservoir to the wound. However, the polymer must first be impregnated with an antimicrobial agent before fabrication of such film. A preferred arrangement of the tapered protuberances includes an ordered arrangement of conical shaped funnels having about 30 to about 1500 tapered protuberances per square inch of topsheel.

Any antimicrobial agent that is compatible with the virgin polymer and will retain its activity after the film fabrication process may be used in this preferred embodiment.

A large number of antimicrobial agents are contemplated for use in the present invention including:
i) metal salts such as silver, copper salts;
ii) typical antibiotics such as neomycin, soframycin, bacitracin;
iii) quaternary ammonium compounds such as centrimide; and
iv) 2,4,4'-trichloro-2'-hydroxydiphenyl ether and 5-chloro-2 (2,4-dichlorophenoxy) phenol available from Microban Products.

In the preferred embodiment, the antimicrobial agent of choice is 2,4,4'-trichloro-2'-hydroxydiphenyl ether.

The porous film should be impregnated with an effective amount of the antimicrobial agent such that the growth of microorganisms is substantially inhibited. The antimicrobial agent is preferably present in the porous polymeric film in an amount from about 0.01% to about 25% by weight of the polymeric material, more preferably between about 1 and 10% by weight.

Figure 6:
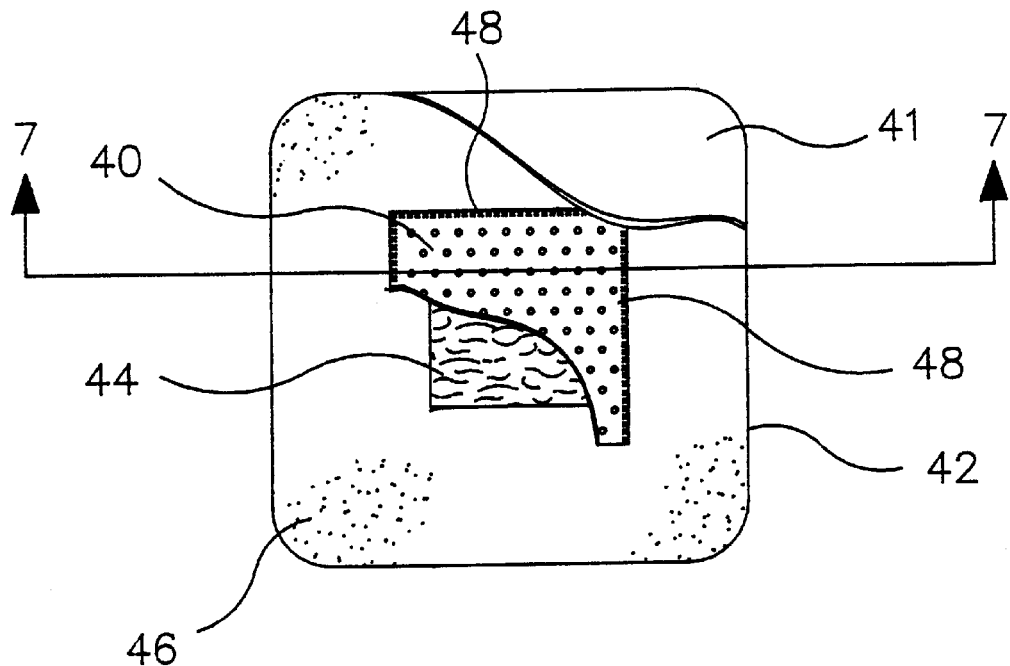
FIG. 6 is a bottom view of an alternative embodiment of the multi-layer island dressing for placement on the wound.
Figure 7:
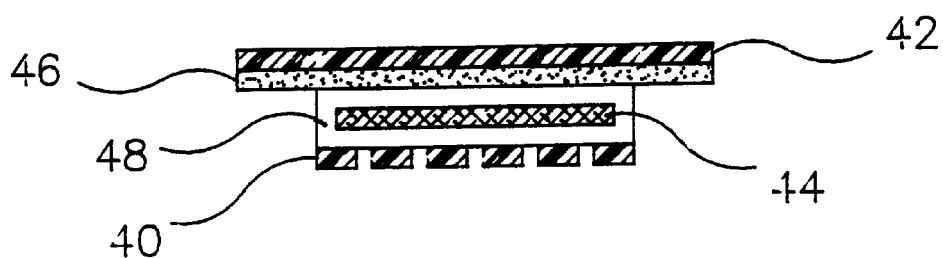
FIG. 7 is an enlarged cross-sectional view of the alternative embodiment of the multi-layer dressing taken along lines 7—7 of FIG. 6.

In an alternative embodiment of the present invention shown in FIGS. 6 and 7, the multi-layer medical dressing may have an outer layer 42, a first layer 40 joined to the outer layer to form a sealed interior reservoir compartment 48 and an absorbent material 44 positioned between the outer layer and first layer. An adhesive layer 46 is coated on a portion of the bottom surface of the outer layer for adherence to the skin surface surrounding the wound.

The outer layer 42 is a continuous semipermeable polymeric film. Representative examples include the semipermeable films as described above. The first layer 40 comprises a non-absorbent, non-adhering porous polymeric film which is impregnated with an antimicrobial agent. Antimicrobial agents which may be incorporated into the polymer include those from groups (i–iv) as described above. In the preferred embodiment, the antimicrobial agent of choice is 2,4,4'-trichloro-2'-hydroxydiphenyl ether.

The porous film should be impregnated with an effective amount of the antimicrobial agent such that the growth of microorganisms is substantially inhibited. The antimicrobial agent is preferably present in the porous polymeric film in an amount from about 0.01% to about 25% by weight of the polymeric material, more preferably between about 1 and 10% by weight.

The polymeric material wherein the antimicrobial agent is homogeneously dispersed includes materials such as low and high density polyethylene, polypropylene, polyurethane, polybutadiene, polyester, polyvinyl chloride, polyolefin copolymers such as ethylene-vinyl acetate copolymers and the like. In a particularly preferred embodiment, the polymeric material is either polyethylene or polyurethane having a thickness from about 0.5 to about 3 mil and preferably from about 1 to about 2 mil.

The porous polymeric film may include webs, netting, perforated film or film having one-way tapered protuberances. The porous film employed in the present invention may be flexible, conformable to anatomical shapes and provide a pathway for passage of wound exudate away from the wound site. The pores or perforations should be sufficient in size to permit wound exudate to move away from the wound site without pooling at the wound.

The edges of first layer 40 are joined or attached to outer layer 42 by heat sealing or other methods of joining discussed earlier. The securing of the first layer to the outer layer forms a sealed interior reservoir compartment 48 thereby restricting outward flow of exudate.

A layer of absorbent material 44 may be included in the sealed interior reservoir compartment 48 in a sufficient amount to collect and hold wound exudate. Absorbent material useful in the present invention may include those described above.

Figure 8:
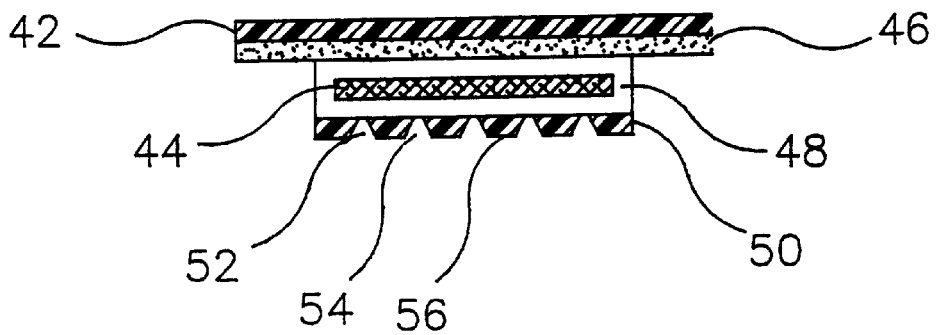
FIG. 8 is an enlarged cross-sectional view of the alternative embodiment multi-layer dressing showing an alternative first layer using one-way film with apertures.
Figure 9:
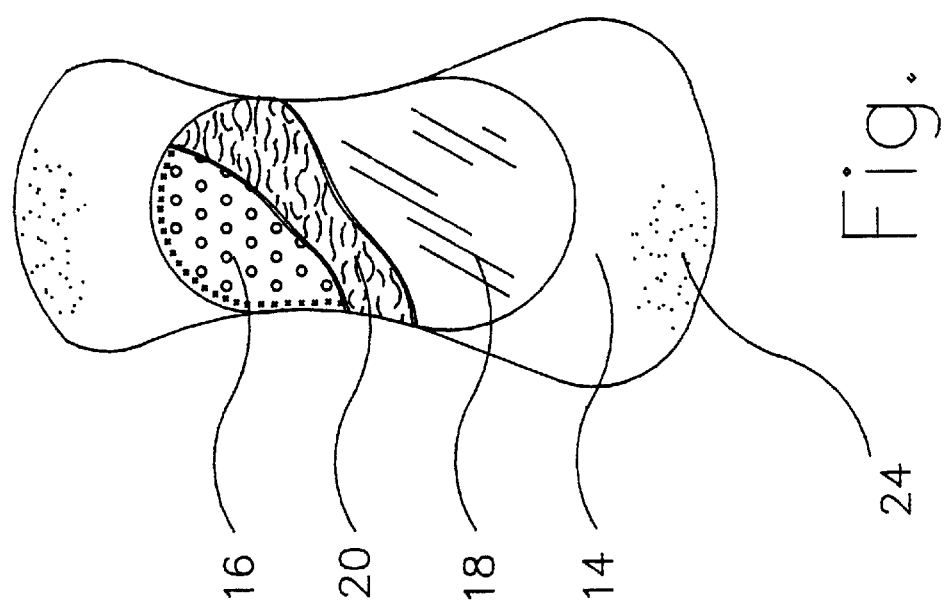
FIGS. 9 and 10 show modified shapes of the multi-layer island dressing of the present invention.
Figure 10:
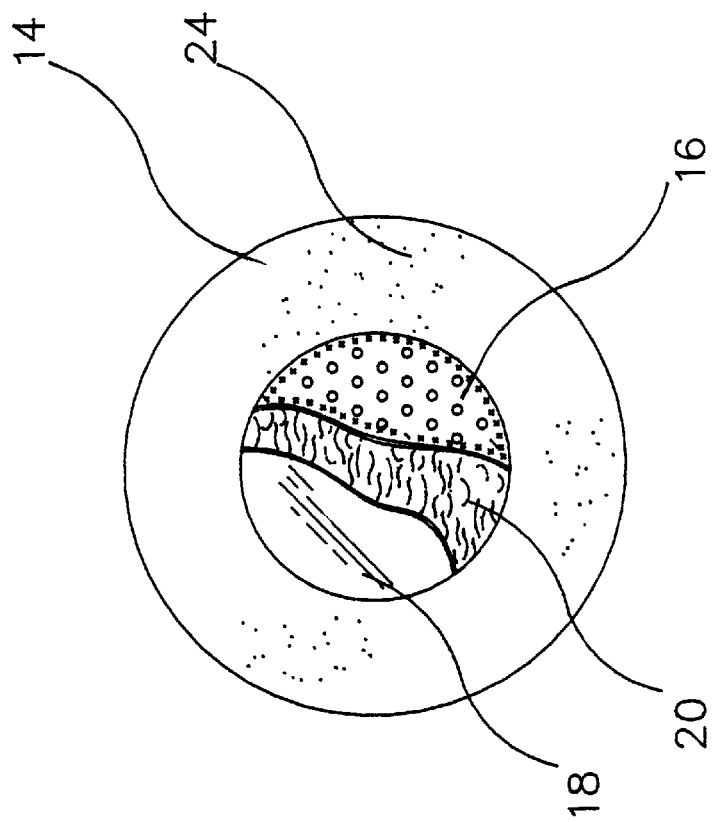

This embodiment may also include first layer 50 comprising a non-absorbent, non-adhering porous one-way polymeric film as shown in FIG. 8. The one-way porous film has a plurality of tapered protuberances 56 having a generally funnel-like configuration which narrow in the direction of the fluid reservoir. These conical pores provide for passage of wound exudate through the larger pore opening 54 into the fluid reservoir 48 between the first 50 and outer layer 42 while the narrowing of the pore at 52 reduces backflow of fluid from the reservoir to the wound site.

Figure 12:
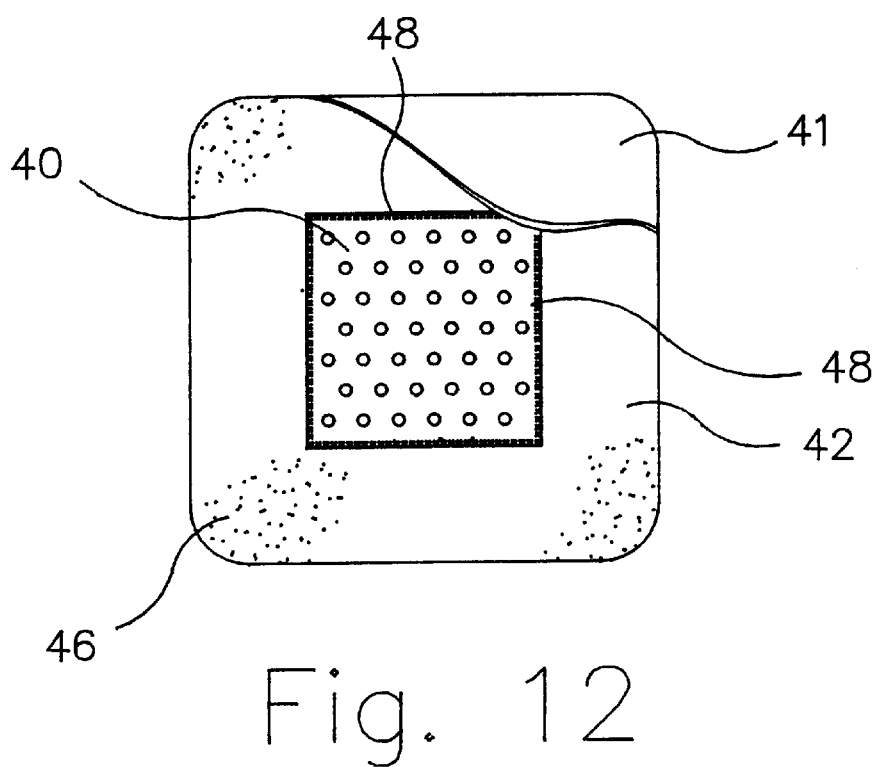
FIG. 12 is a bottom view of an alternative embodiment of the multi-layer island dressing for placement on the wound without an absorbent material insert in the fluid reservoir.

For wounds that are releasing a minimum of exudate, this embodiment may eliminate the absorbent material insert in the absorbent assembly such as shown in FIG. 12. Instead, the one-way film having tapered capillaries provide pathways for drainage into the fluid reservoir and provide sufficient retention of the exudate by substantially and substantially restrict backflow to the wound site. The body fluid is retained in the fluid reservoir and away from the wound bed.

The dressings of the present invention as shown in the illustrations are generally square, however, the configuration is not critical and they may be any desired size or shape, e.g. oval, rectangular, circular (shown in FIG. 10), and the like. For example, referring to FIG. 9, there is shown a dressing used for covering a movable joint such as an elbow or knee. Depending on the size and use the embodiments of the present invention may be applied to limbs or the central trunk of a patient. These dressings may include or eliminate the absorbent material in the fluid reservoir compartment depending on the anticipated bodily fluids discharged from the wound site. The absorbent assembly may be positioned in the central region of the outer layer or may be offset depending on the application. Furthermore, the absorbent material may incorporate an antimicrobial agent to increase defenses against microorganisms. Still further, it is contemplated by the inventors that the polymeric films utilized in the present invention may be transparent, opaque, or embossed.

While specific materials and details of construction are referred to in connection with the description of the illustrated embodiments, it will be understood that equivalent materials and other details of construction may be resorted to within the spirit of the invention hereinafter claimed.

What is claimed is:

1. A multi-layer medical island dressing providing antimicrobial protection comprising:
   a) an absorbent assembly including;
      i) a first layer comprising a non-absorbent, non-adhering porous flexible polymeric film, said first layer having a wound contacting side and an opposing non-wound contacting side, said non-absorbent, non-adhering porous flexible polymeric film having impregnated therethrough an antimicrobial agent;
      ii) a second layer comprising a continuous semipermeable polymeric film, said second layer is joined to said non-wound contacting side of said first layer to form a sealed interior reservoir compartment;
      iii) an absorbent material positioned between said first and second layer in said sealed interior reservoir compartment for retaining exudate discharged from a wound; and
   b) an outer layer comprising a gas permeable continuous polymeric film, said outer layer having a bottom surface for contacting an area around said wound and an opposing top surface, said bottom surface positioned adjacent to said second layer of the absorbent assembly and extending beyond said absorbent assembly, said outer layer having at least a portion of said bottom surface coated with an adhesive material for adhering to said area around said wound.

2. The multi-layer dressing according to claim 1 wherein said antimicrobial agent is a member selected from the group consisting of metal salts, neomycin, soframycin, bacitracin, quaternary ammonium compounds, and 2,4,4'-trichloro-2'-hydroxydiphenyl ether.

3. The multi-layer dressing according to claim 1 wherein said antimicrobial agent is 2,4,4'-trichloro-2'-hydroxydiphenyl ether.

4. The multi-layer dressing according to claim 3 wherein said first layer is impregnated with said antimicrobial agent in an amount from about 0.01 to about 25% by weight of said polymeric film.

5. The multi-layer dressing according to claim 1 wherein said non-absorbent, non-adhering porous film layer comprises a compound selected from the group consisting of polyurethane and polypropylene.

6. The multi-layer dressing according to claim 1 wherein said semipermeable continuous polymeric film of said second layer has a moisture vapor permeability of at least 1000 grams per square meter per 24 hours at an 80% relative humidity differential at 40° C.

7. The multi-layer dressing according to claim 1 wherein said absorbent material is a member selected from the group consisting of cotton, rayon, pulp products, superabsorbents webs, foams, and fibers.

8. The multi-layer dressing according to claim 1 wherein said absorbent assembly is centrally positioned adjacent to said outer layer.

9. A multi-layer medical island dressing providing antimicrobial protection comprising:
   a) an absorbent assembly including;
      i) a first layer comprising a non-absorbent, non-adhering porous one-way polymeric film impregnated with an antimicrobial agent, said porous one-way polymeric film having a plurality of tapered protuberances, said first layer having a wound contacting side and an opposing non-wound contacting side, said non-absorbent, non-adhering porous one-way polymeric film having impregnated therethrough an antimicrobial agent;
      ii) a second layer comprising a semipermeable polymeric film, said second layer joined to said non-wound contacting side of said first layer to form a sealed interior reservoir compartment;
      iii) an absorbent material positioned between said first and second layer in said sealed interior reservoir compartment for retaining exudate from a wound; and
   b) an outer layer comprising a gas permeable continuous polymeric film, said outer layer having a bottom surface for contacting an area around the wound and an opposing top surface, said bottom surface positioned adjacent to said second layer of said absorbent assembly and extending beyond said absorbent assembly, said outer layer having at least a portion of said bottom surface coated with an adhesive material for adhering to said area around said wound.

10. The multi-layer dressing according to claim 9 wherein said antimicrobial agent is a member selected from the group consisting of metal salts, neomycin, soframycin, bacitracin, quaternary ammonium compounds, and 2,4,4'-trichloro-2'-hydroxydiphenyl ether.

11. The multi-layer dressing according to claim 9 wherein said antimicrobial agent is 2,4,4'-trichloro-2'-hydroxydiphenyl ether.

12. The multi-layer dressing according to claim 11 wherein said first layer is impregnated with said antimicrobial agent in an amount from about 0.01 to about 25% by weight of the film.

13. The multi-layer dressing according to claim 9 wherein said non-absorbent, non-adhering porous film layer comprises a compound selected from the group consisting of polyurethane and polypropylene.

14. The multi-layer dressing according to claim 9 wherein said semipermeable continuous polymeric film of said second layer has a moisture vapor permeability of at least 1000 grams per square meter per 24 hours at an 80% relative humidity differential at 40° C.

15. The multi-layer dressing according to claim 9 wherein said absorbent material is a member selected from the group consisting of cotton, rayon, pulp products, superabsorbents webs, foams, and fibers.

16. A multi-layer dressing providing antimicrobial protection comprising:
   a) an absorbent assembly including;
      i) a first layer comprising a non-absorbent, non-adhering porous one-way polymeric film impregnated with an antimicrobial agent, said porous one-way polymeric film having a plurality of tapered protuberances, said first layer having a wound contacting side and an opposing non-wound contacting side, said non-absorbent, non-adhering porous one-way polymeric film having impregnated therethrough an antimicrobial agent;
      ii) a second layer comprising a semipermeable polymeric film, said second layer joined to said non-wound contacting side of said first layer to form a sealed interior reservoir compartment; and
   b) an outer layer comprising a gas permeable continuous polymeric film, said outer layer having a bottom surface for contacting an area around a wound and an opposing top surface, said bottom surface positioned adjacent to said second layer of said absorbent assembly and extending beyond said absorbent assembly, said outer layer having at least a portion of said bottom surface coated with an adhesive material for adhering to said area around said wound.

17. The multi-layer dressing according to claim 16 wherein said antimicrobial agent is 2,4,4'-trichloro-2'-hydroxydiphenyl ether.

18. The multi-layer dressing according to claim 17 wherein said porous one-way polymeric film is impregnated with said antimicrobial agent in an amount from about 0.01 to about 25% by weight of the film.

19. The multi-layer dressing according to claim 16 wherein said non-absorbent, non-adhering porous film layer comprises a compound selected from the group consisting of polyurethane and polypropylene.

20. A multi-layer medical island dressing providing antimicrobial protection comprising:
   a) a first layer comprising a non-absorbent, non-adhering porous flexible polymeric film, said non-absorbent, non-adhering porous flexible polymeric film having impregnated therethrough an antimicrobial agent, said first layer/ having a wound contacting side and an opposing non-wound contacting side;
   b) an outer layer comprising a semipermeable continuous polymeric film, said outer layer having a bottom surface for contacting an area around a wound and an opposing top surface, said bottom surface of said outer layer joined to said non-wound contacting side of said first layer to form a sealed interior reservoir compartment, said outer layer extending beyond said first layer and having at least a portion of said bottom surface coated with an adhesive material for adhering to said area around said wound.

21. The multi-layer dressing according to claim 20 further comprising an absorbent material positioned between said first and outer layer in said sealed interior reservoir compartment for retaining exudate from said wound.

22. The multi-layer dressing according to claim 21 wherein said antimicrobial agent is 2,4,4'-trichloro-2'-hydroxydiphenyl ether.

23. The multi-layer dressing according to claim 22 wherein said first layer is impregnated with said antimicrobial agent in an amount from about 0.01 to about 25% by weight of the film material.

24. The multi-layer dressing according to claim 21 wherein said non-absorbent, non-adhering porous film layer comprises a compound selected from the group consisting of polyurethane and polypropylene.

25. The multi-layer dressing according to claim 21 wherein said semipermeable continuous polymeric film of said second layer has a moisture vapor permeability of at least 1000 grams per square meter per 24 hours at an 80% relative humidity differential at 40° C.

26. The multi-layer dressing according to claim 20 wherein said porous flexible polymeric film impregnated with said antimicrobial agent is porous one-way polymeric film having a plurality of tapered protuberances.

27. The multi-layer dressing according to claim 21 wherein said porous flexible polymeric film impregnated with said antimicrobial agent is porous one-way polymeric film having a plurality of tapered protuberances.

28. A multi-layer dressing providing antimicrobial protection comprising:
   a) a first layer comprising a non-absorbent, non-adhering porous flexible polymeric film;
   b) an antimicrobial agent incorporated into said first layer;
   c) an outer layer comprising a semipermeable continuous polymeric film; and
   d) an interior reservoir compartment formed by joining said first layer to said outer layer to form an interior reservoir compartment.

29. The multi-layer dressing according to claim 28 wherein the antimicrobial agent is 2,4,4'-trichloro-2'-hydroxydiphenyl ether in an amount from about 0.01 to about 25% by weight of said polymeric film.

30. The multi-layer dressing according to claim 28 further comprising absorbent material positioned within the interior reservoir compartment.

31. The multi-layer dressing according to claim 28 wherein the porous polymeric film has a plurality of tapered protuberances.

* * * * *